(12) United States Patent
Zeeff

(10) Patent No.: US 7,018,212 B2
(45) Date of Patent: Mar. 28, 2006

(54) ARTIFICIAL BONE

(75) Inventor: Mike Zeeff, Grand Haven, MI (US)

(73) Assignee: Medical Accessories & Research Corporation, Zeeland, MI (US)

( * ) Notice: Subject to any disclaimer, the term of this patent is extended or adjusted under 35 U.S.C. 154(b) by 0 days.

(21) Appl. No.: 10/616,705

(22) Filed: Jul. 10, 2003

(65) Prior Publication Data

US 2004/0082997 A1    Apr. 29, 2004

Related U.S. Application Data

(60) Provisional application No. 60/412,274, filed on Sep. 21, 2002.

(51) Int. Cl.
*G09B 23/28* (2006.01)

(52) U.S. Cl. .................................... 434/274

(58) Field of Classification Search ................ 434/262, 434/267, 274, 295; 623/23.56, 23.61, 23.58, 623/23.59
See application file for complete search history.

(56) References Cited

U.S. PATENT DOCUMENTS

| | | | |
|---|---|---|---|
| 2,472,819 A | 6/1949 | Giesen | |
| 2,483,034 A | 9/1949 | Braeg | |
| 2,988,823 A | 6/1961 | Rosenbloom | |
| 2,995,833 A | 8/1961 | Bezark | |
| 4,106,219 A * | 8/1978 | Schneider et al. | 434/274 |
| 4,200,995 A * | 5/1980 | Trella | 434/274 |
| 4,314,380 A * | 2/1982 | Miyata et al. | 623/23.61 |
| 4,451,416 A | 5/1984 | Burtscher | |
| 4,838,795 A * | 6/1989 | Draenert | 434/274 |
| 5,082,803 A * | 1/1992 | Sumita | 501/1 |
| 5,092,888 A * | 3/1992 | Iwamoto et al. | 623/23.58 |
| 5,607,311 A | 3/1997 | Browne-Wilkinson | |
| 5,672,059 A | 9/1997 | Browne-Wilkinson | |
| 6,008,430 A * | 12/1999 | White | 623/23.5 |
| 6,116,911 A | 9/2000 | Biermann et al. | |
| 6,206,703 B1 | 3/2001 | O'Bannon | |
| 6,379,725 B1 * | 4/2002 | Wang et al. | 426/72 |
| 6,471,519 B1 * | 10/2002 | Biermann et al. | 434/274 |
| 6,520,775 B1 * | 2/2003 | Lee | 434/263 |

* cited by examiner

*Primary Examiner*—Kurt Fernstrom
(74) *Attorney, Agent, or Firm*—Watson IP Group, PLC; Jovan N. Jovanovic

(57) ABSTRACT

An artificial bone comprising a substrate material and at least one of a suppression component and an x-ray component. The substrate material comprises a plurality of closed cells. The suppression component is impregnated into at least one of the plurality of closed cells. The x-ray component is dispersed within the substrate material. The invention further comprises a method of manufacturing same.

13 Claims, 1 Drawing Sheet

ARTIFICIAL BONE

CROSS-REFERENCE TO RELATED APPLICATION

This application claims the benefit of U.S. Provisional Patent Application Ser. No. 60/412,274 entitled "Artificial Bone" which was filed Sep. 21, 2002. The disclosure of the provisional application is incorporated herein in its entirety.

BACKGROUND OF THE INVENTION

1. Field of the Invention

The present invention relates in general to an artificial bone, and more particularly, to a non-implantable, artificial bone which can be utilized for, among other things, demonstration and/or educational purposes.

2. Background Art

Artificial bones have been known in the art for several years and are the subject of numerous United States Patents, including: U.S. Pat. No. 6,206,703 B1 entitled "Biofidelic Human Seating Surrogate Apparatus;" U.S. Pat. No. 6,116,911 entitled "Bone Substitute For Training And Testing;" U.S. Pat. No. 5,672,059 entitled "Orthopaedic Human Skeletal Demonstration Aids;" U.S. Pat. No. 5,607,311 entitled "Orthopaedic Human Skeletal Demonstration Aids;" U.S. Pat. No. 4,451,416 entitled Method Of Producing A Composite Foamed Resin Torso And Head Section Of A Human Summary For Medical Training Purposes;" U.S. Pat. No. 4,106,219 entitled "Plastic Bone Used For Training Purposes By Surgeons;" U.S. Pat. No. 2,995,833 entitled "Anatomical Device;" U.S. Pat. No. 2,988,823 entitled "Transparent Anatomical Model;" U.S. Pat. No. 2,483,034 entitled "Anatomical Instruction Device;" and U.S. Pat. No. 2,472,819 entitled "Mechanical Skeleton," all of which are hereby incorporated herein by reference in their entirety. While such bones are known, there has been a constant struggle to improve the mechanical properties and the realism of the bones, to, in turn, increase the utility and the usefulness thereof for exemplary purposes.

One particularly problematic issue with conventional artificial bones is that when the bones are drilled, tapped, and/or gouged by hand or powered instruments, an undesirable amount of dust and/or debris is generated. Such dust and debris is rather unrealistic, as real bone does not exhibit such properties. Moreover, the debris and dust, obstructs or otherwise impairs viewing of the demonstrated procedure. As such, the usefulness of the artificial bone is compromised.

Another particularly problematic issue with conventional artificial bones is that the bones are generally penetrated by x-rays. As such, conventional artificial bones are of little utility for the purposes of instructing individuals as to the reading of x-ray films. Certain artificial bones have been coated or painted in a metal based material which absorbs x-rays. While such artificial bones are an improvement, the coatings and paintings generally alter the underlying artificial bone, and the realism of the bone is compromised in various operational capacities.

It is therefore an object of the present invention to provide an artificial bone which more accurately represents a real bone.

It is another object of the present invention to provide an artificial bone which exhibits desired mechanical properties during cutting, chipping, gouging, drilling, tapping, and when undergoing other material removing processes.

It is another object of the present invention to provide an artificial bone which reacts realistically under an x-ray procedure.

These and other objects will become apparent in light of the specification and claims appended hereto.

SUMMARY OF THE INVENTION

The present invention is directed to an artificial bone. The artificial bone comprises a substrate material and at least one of a suppression component and an x-ray component. The substrate material comprises a plurality of closed cells. The suppression component is impregnated into at least one of the plurality of closed cells. The x-ray component dispersed within the substrate material.

In a preferred embodiment, the artificial bone further includes each of the suppression component and the x-ray component.

In another preferred embodiment, the suppression component comprises a polyurethane material having a plurality of closed cells. Preferably, the substrate material comprises one of the group consisting of: polyethylene, polypropylene and polymeric resins.

In another preferred embodiment, the x-ray component comprises a plurality of barium components. Preferably, the x-ray component comprises approximately 10% by weight of the substrate material.

In yet another preferred embodiment, the suppression component comprises a propylene glycol material. Preferably, the substrate material comprises one of the group consisting of: water, ethylene glycol, oils, polar and non-polar solvents, lotions and mixtures thereof.

The invention further comprises a method of manufacturing an artificial bone. The method comprises the steps of: providing a substrate base material; optionally mixing an x-ray component into the substrate base material; curing the substrate base material into a substrate; and optionally impregnating the substrate with a suppression component. At least one of the steps of mixing and impregnating are executed such that the resulting artificial bone includes at least one of the x-ray component and the suppression component.

In one embodiment of the method, the step of impregnating comprises the steps of: placing the substrate within an autoclave; introducing the suppression component; and elevating the pressure within the autoclave for a predetermined period of time.

In another embodiment of the method, the method further comprises the step of placing the substrate base material into a mold prior to the step of curing.

In yet another embodiment, the method further includes the step of finishing the outer surface of the substrate after the step of curing.

In another embodiment of the invention, each of the steps of mixing and impregnating are executed such that the resulting artificial bone includes each of the x-ray component and the suppression component.

BRIEF DESCRIPTION OF THE DRAWING

The invention will now be described with reference to the drawing wherein.

DETAILED DESCRIPTION OF THE INVENTION

Figure 1:
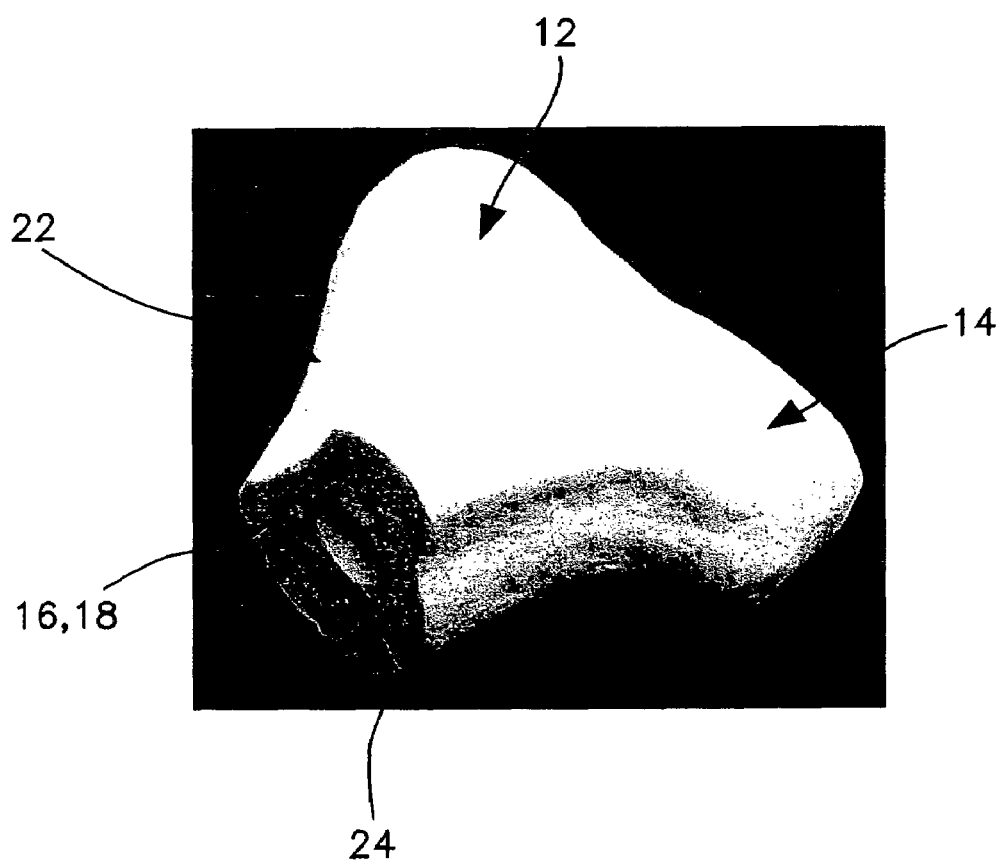
FIG. 1 of the drawings a perspective view of a portion of a bone fabricated in accordance with the present invention, wherein the bone has been severed to show a cross-sectional configuration.

While this invention is susceptible of embodiment in many different forms, there is shown in the drawing and will herein be described in detail several specific embodiments with the understanding that the present disclosure is to be considered as an exemplification of the principles of the invention and is not intended to limit the invention to the embodiments illustrated.

It will be understood that like or analogous elements and/or components, referred to herein, may be identified throughout the drawings with like reference characters.

Referring now to the drawing and to FIG. 1 in particular, artificial bone is shown generally at 12. As will be explained in greater detail below, artificial bone 12 exhibits substantially enhanced simulated realism, mechanical properties, as well as substantially diminished cracking, chipping, and/or dust generation due to their novel fabricated composition and associated process for preparing the same.

For purposes of background, conventional artificial bones may be fabricated from a polyurethane resin, one of which is commercially available from BayOne Urethane Systems, LLC (formerly known as PolyOne) part number POLY RF1855-4LB and ISO 2000Y. The polyurethane resin constituents are mixed as directed and poured into a mold. After approximately eight minutes, the cured polyurethane substrate is removed from the mold for final trimming and finishing using conventional techniques. As was previously discussed, artificial bones fabricated in accordance with such a conventional method, exhibit a plurality of poor, undesirable, physical characteristics—including, but not limited to, cracking, chipping, and/or excessive dust generation. Moreover, such bones are not suitable for use in an x-ray machine, as x-rays generally penetrate such a material.

In comparison, bone 12 shown in FIG. 1 comprises substrate 14 and suppression component 16, and x-ray component 18. While a partial bone is shown in FIG. 1, for purposes of illustration, it is contemplated that bone 12 is preferably sized and shaped so as to substantially mimic a bone of an animal or a human. Of course, the invention is not limited to any particular bone or set of bones, and, it is contemplated that the invention has broad application relative to a number of different bones of both humans and other animals.

Substrate 14 is shown as comprising a polyurethane material, such as the material described above relative to conventional bones, which when cured includes outer shell 22 and inner cells 24 (many of which are closed cells). Such material generally comprises a cured substrate base material which is the result of a chemical reaction of constituents. Of course, other materials are likewise contemplated for use. In particular, such materials may include, but are not limited to, polyethylene, polypropylene, polymeric resins as well as other materials which are at least partially closed celled. The polyurethane material, while exemplary only, comprises what has become a material of choice for the fabrication of artificial bones.

Suppression component 16 comprises a propylene glycol which is impregnated into the bones after the curing process. In certain embodiments, the suppression component can be combined with a dye (such as a red dye) to indicate the presence of a suppression component within the substrate. While a propylene glycol material is contemplated for use, it is likewise contemplated that other materials may be utilized, including but not limited to, water, ethylene glycol, oils, polar and non-polar solvents, lotions, mixtures thereof, among others.

X-ray component 18 is shown in FIG. 1 as comprising a plurality of small sized components (i.e., granular, particulate and/or powder) which are mixed into the substrate. The components are sized so as to be readily able to mix with the substrate. The x-ray component is, through mixing, substantially dispersed through the substrate. One such material comprises barium components, which have been ground to a powder. As will be understood to one of skill in the art, barium is a material which readily absorbs x-rays to a desired extent. Of course, other materials which absorb x-rays, and which are capable of being integrated into the substrate are likewise contemplated for use (barium generally does not adversely affect operation of the suppression component). Such materials may include, but are not limited to other metals, such as other heavy metals, among others. Of course, other means by which the x-ray component may be introduced into the substrate (i.e., co-molding, impregnating, etc.) are likewise contemplated.

It will be understood that in certain preferred embodiments, the x-ray component may be utilized without the suppression component. Such embodiments are useful when little to no machining is undertaken, but the properties of bones and the response thereof to x-rays is investigated. In other embodiments, the suppression component may be utilized without the x-ray component. Such a structure is particularly useful wherein the artificial bone will undergo machining processes, but wherein x-ray properties are not relevant.

Artificial bone 12 of the present invention is fabricated using the following process. First, the substrate base material is mixed as directed. During the mixing step, the x-ray component is added to the mixture. In one embodiment, the x-ray component comprises barium powder which comprises about 10 wt % of the substrate material. Once fully mixed, the x-ray component is generally dispersed substantially throughout the substrate. The combination substrate and x-ray component is poured into a mold which is configured to render a bone of the desired configuration and dimension.

The combination substrate and x-ray component remain in the mold until the substrate is fully, or substantially fully cured (i.e., until the final shape is substantially retained). As such, after approximately eight minutes, the polyurethane is removed from the mold for final trimming and finishing using conventional techniques. Such conventional techniques include cutting, grinding, polishing and sanding, among others.

Once formed, the fabricated bone is placed into a pressure tank (autoclave). Subsequently, the suppression component (with optional dye) is introduced to submerge the bone. In the particular embodiment disclosed, propylene glycol tinted with red dye is introduced to submerge the bone. The pressure within the autoclave is raised, wherein the suppression component is forced into the closed cells of substrate 14. Once complete, the resulting bone is removed from the autoclave and the excess propylene glycol allowed for drain off from the exterior of the artificial bone.

The particular time and pressure may depend on the materials used for the suppression component and the substrate, in the embodiment disclosed, the substrate remained in the autoclave for seven minutes at an elevated pressure of 90 psi.

Once fabricated, the physical characteristics of artificial bone 12 was tested and remarkable improvements in dust reduction, chipping, as well as cracking were observed. Also, the bone was capable of absorbing x-rays to a predetermined extent, so as to render an image on conventional x-ray equipment, due to the x-ray component which was added to the substrate prior to curing. In addition, artificial bone 12 exhibited a substantial improvement in realism and feel.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. An artificial bone comprising:
    a substrate material, wherein the substrate material comprises a molded polymer having a plurality of closed cells; and
    a suppression component which limits dusting, chipping and cracking of the substrate material, the suppression component impregnated into at least one of the plurality of closed cells.

2. The artificial bone of claim 1 further comprising an x-ray component dispersed within the substrate material in a quantity sufficient to render the artifical bone substantially opaque to an x-ray.

3. The artificial bone of claim 1 wherein the substrate material comprises a polyurethane material having a plurality of closed cells.

4. The artificial bone of claim 1 wherein the substrate material comprises one of the group consisting of: polyethylene, polypropylene and polymeric resins.

5. The artificial bone of claim 2 wherein the x-ray component comprises a plurality of barium components.

6. The artificial bone of claim 2 wherein the x-ray component comprises 10% by weight of the substrate material such that the quantity of x-ray component is sufficient to render the artificial bone substantially opaque to an x-ray.

7. The artificial bone of claim 1 wherein the suppression component comprises a propylene glycol material.

8. The artificial bone of claim 1 wherein the suppression component comprises one of the group consisting of: water, ethylene glycol, oils, polar and non-polar solvents, lotions and mixtures thereof.

9. A method of manufacturing an artificial bone comprising the steps of:
    providing a substrate base material, the substrate base material comprising a polymer;
    curing the substrate base material into a substrate; and
        impregnating the substrate with a suppression component, to, in turn, provide an artificial bone which limits dusting, chipping and cracking of the substrate material.

10. The method of claim 9 wherein the step of impregnating comprises the steps of:
    placing the substrate within an autoclave;
    introducing the suppression component; and
    elevating the pressure within the autoclave for a predetermined period of time.

11. The method of claim 9 further comprising the step of placing the substrate base material into a mold prior to the step of curing.

12. The method of claim 9 further comprising the step of finishing the outer surface of the substrate after the step of curing.

13. The method of claim 9 further comprising the step of mixing an x-ray component into the substrate material prior to the step of curing in an amount sufficient to render the artificial bone opaque to an x-ray.

* * * * *